(12) United States Patent
Noda et al.

(10) Patent No.: US 6,949,689 B2
(45) Date of Patent: Sep. 27, 2005

(54) ABSORBENT ARTICLE

(75) Inventors: Akira Noda, Tochigi (JP); Koji Kanazawa, Tochigi (JP); Akihiko Gunji, Tochigi (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 09/818,783

(22) Filed: Mar. 28, 2001

(65) Prior Publication Data

US 2001/0044611 A1 Nov. 22, 2001

(30) Foreign Application Priority Data

Apr. 19, 2000 (JP) .................................... 2000-118469

(51) Int. Cl.$^7$ ............................................. A61F 13/15
(52) U.S. Cl. ..................................................... 604/361
(58) Field of Search ................................ 604/361–362, 604/378

(56) References Cited

U.S. PATENT DOCUMENTS

| | | | |
|---|---|---|---|
| 5,133,707 A | | 7/1992 | Rogers et al. |
| 5,458,590 A | * | 10/1995 | Schleinz et al. ............. 101/483 |
| 5,766,212 A | * | 6/1998 | Jitoe et al. .................... 604/361 |
| 5,883,028 A | * | 3/1999 | Morman et al. ............. 156/229 |
| 2001/0031954 A1 | * | 10/2001 | Jordan et al. ................ 604/385.01 |

FOREIGN PATENT DOCUMENTS

| | | |
|---|---|---|
| GB | 2293573 A | 4/1996 |
| JP | 7-313549 A | 12/1995 |
| JP | 9-140742 A | 6/1997 |
| JP | 9-309169 A | 12/1997 |
| JP | 1010877 | 4/1998 |
| JP | 10-506586 A | 6/1998 |
| JP | 11-151785 A | 6/1999 |
| TW | 347323 | 12/1998 |
| WO | WO 9960973 | 2/1999 |
| WO | WO 99/16401 | 4/1999 |
| WO | WO 00/38915 | 7/2000 |

* cited by examiner

Primary Examiner—Larry I. Schwartz
Assistant Examiner—C. Lynne Anderson
(74) Attorney, Agent, or Firm—Birch, Stewart, Kolasch & Birch, LLP

(57) ABSTRACT

An absorbent article 1 comprising a topsheet 2, a backsheet 3, and an absorbent member 4 is disclosed. The backsheet 3 comprises a laminated sheet composed of a breathable film 3a printed with a multicolor pattern 10 and nonwoven materials 3b and 3c superposed on the printed side of the film 3a. The printed area of the film has an L* value of 10 to 93 and a C* value of 20 to 120 as measured with a color difference meter. The nonwoven materials 3b and 3c have a light transmittance of 40 to 83%.

4 Claims, 1 Drawing Sheet

ABSORBENT ARTICLE

BACKGROUND OF THE INVENTION

The present invention relates to an absorbent article having a breathable backsheet which is printed in multicolor and has a cloth-like appearance and feel.

Absorbent articles such as disposable diapers have a composite sheet comprising a breathable film and a nonwoven material as a backsheet in order to prevent an increase of humidity in the internal environment of the article while worn and also to improve the texture or feel to the touch. Some absorbent articles have the backsheet printed with logos or patterns to improve the appearance and to appeal to consumers. For example, the backsheet can be printed in multicolor to find greater consumer acceptance.

The printing could be done on the surface side or the reverse side of the nonwoven material or on the side of the breathable film to be brought into contact with the nonwoven material. Nonwoven material, being an aggregate of fiber, has an uneven surface and is difficult to print in multicolor neatly. The film, on the other hand, has excellent surface characteristics and is fit for high-quality printing. Therefore, multicolor printing is usually done on the film on the side to be laminated with nonwoven material. In this case, however, the print is covered with a laminating nonwoven material and therefore gets blurred to the eyes of consumers. Such blurred printing would rather reduce the consumer acceptance. The clearness of the printing covered with a nonwoven material cannot be improved but by reducing the thickness or basis weight of the nonwoven material, which would make the texture or feel of the product insufficient.

WO99/60973 discloses a disposable diaper having a laminate sheet comprising a breathable film and a nonwoven material, in which the film is printed on its side laminated with the nonwoven material. The object of the invention disclosed is to prevent the background color of the film from yellowing which will reduce consumer acceptance. The invention uses a film whose b* value is in a specific range to achieve the object. The proposed diaper cannot be seen as satisfactory in both clearness of the multicolor printing and the texture or the touch.

SUMMARY OF THE INVENTION

It is therefore an object of the present invention is to provide a multicolor-printed absorbent article which is satisfactory in both clearness of the printing and texture or touch and to provide a backsheet for the absorbent article.

The object of the present invention is accomplished by an absorbent article comprising a liquid-permeable topsheet, a liquid-impermeable backsheet, and a liquid retentive absorbent member interposed between the topsheet and the backsheet, wherein the backsheet comprises a laminated sheet composed of a breathable or water vapor permeable film printed with a multicolor pattern and a nonwoven material, the nonwoven material being superposed on the printed side of the film, the printed area of the film has an L* value of 10 to 93 and a C* value of 20 to 120 as measured with a color difference meter, and the nonwoven material has a light transmittance of 40 to 83%.

The object of the present invention is also accomplished by a backsheet for absorbent articles, which comprises a laminated sheet composed of a breathable film printed with a multicolor pattern and a nonwoven material, the nonwoven material being superposed on the printed side of the film, the printed area of the film having an L* value of 10 to 93 and a C* value of 20 to 120 as measured with a color difference meter, and the nonwoven material having a light transmittance of 40 to 83%.

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
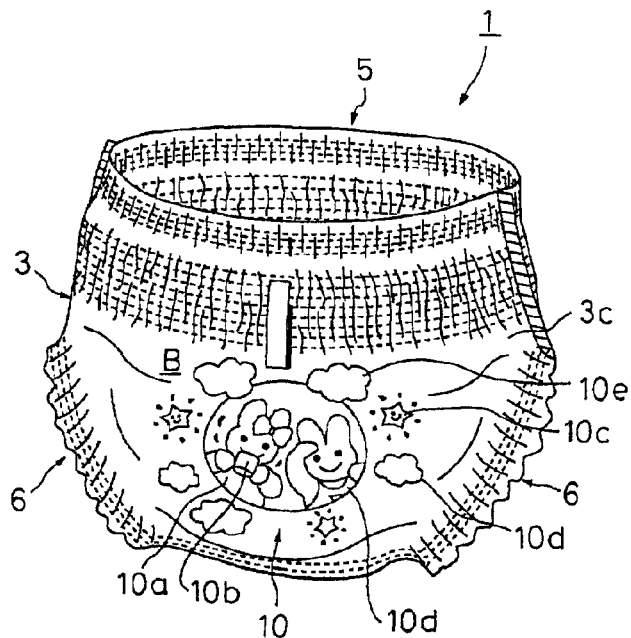
FIG. 1 is a perspective view of a pants type disposable diaper as an embodiment of the absorbent article according to the present invention, seen from the rear side.
Figure 2A:
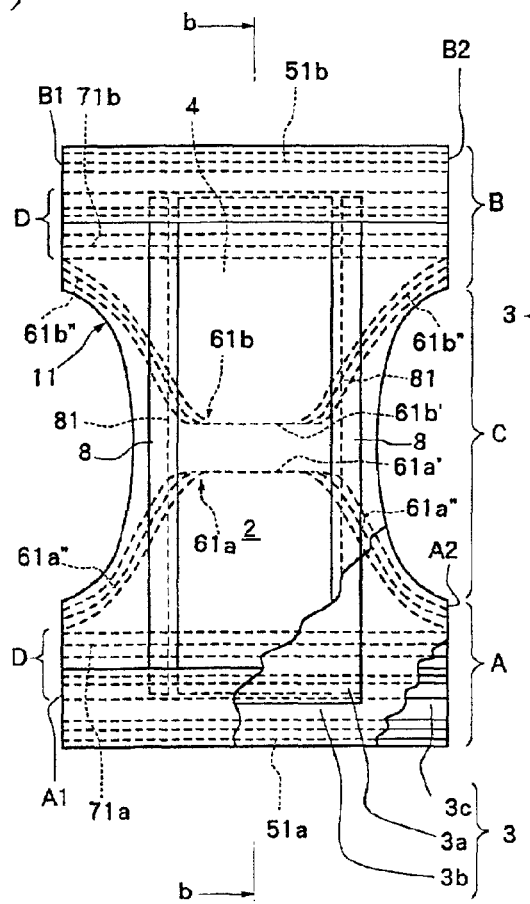
FIG. 2(a) is a plan view of the topsheet side of the pants type disposable diaper of FIG. 1 in its unfolded state, with part thereof cut away.
Figure 2B:
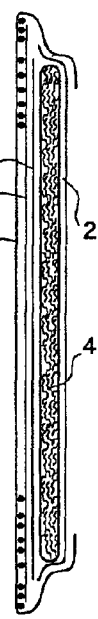
FIG. 2(b) is a cross-section of FIG. 2(a) taken along line b—b.

A preferred embodiment of the present invention will be described with reference to the drawings. FIG. 1 is a perspective viewed from the rear side. FIG. 2(a) is a plan view of the diaper of FIG. 1 in its unfolded state, viewed from the topsheet side thereof, with part of which cut away. FIG. 2(b) is a cross-section of FIG. 2(a) along line b—b.

As shown in FIGS. 1, 2(a) and 2(b), the disposable diaper 1 of this embodiment comprises a liquid-permeable topsheet 2, a liquid-impermeable backsheet 3, and a liquid retentive absorbent member 4 interposed therebetween.

The diaper 1 is divided into a front body portion A, which comes into contact with the wearer's stomach side skin, a rear body portion B, which is on the wearer's back side, and a crotch portion C, which is located between portions A and B. Side ends A1 and A2 of the front body portion A and side ends B1 and B2 of the rear body portion B are joined, respectively, to form a waist opening 5 and a pair of leg openings 6. The joining is carried out by heat sealing, radiofrequency sealing, ultrasonic sealing, and the like.

The absorbent member 4 is almost rectangular. The middle portion of each longer side of the absorbent member 4 is curved inward to its longitudinal center line. The topsheet 2 is also almost rectangular and is slightly larger than the absorbent member 4, extending outward from all the edges of the absorbent member 4. The topsheet 2 can be of the same type as commonly used in the art of disposable diapers. The absorbent member 4 comprises superabsorbent polymer particles and a fibrous material and enveloped in tissue (not shown).

The backsheet 3 comprises a breathable or water vapor permeable film 3a, a first nonwoven material 3b superposed on the breathable film 3a, and a second nonwoven material 3c superposed on the first nonwoven material 3b as an outer surface of the diaper 1.

The breathable film 3a in the backsheet 3 has an almost rectangular shape which is slightly larger than the absorbent member 4, extending outward from all the edges of the absorbent member 4, similarly to the topsheet 2. The two nonwoven materials 3b and 3c in the backsheet 3 are the same shape and size, and of a shape and a size and larger than the breathable film 3a, extending outward from all the edges of the film 3a. The nonwoven materials 3b and 3c also have its middle portion curved inward to make a sandglass shape. The three of the breathable film 3a, the nonwoven material 3b, and the nonwoven material 3c are jointed together into a unitary laminate by an appropriate joining means, such as a hot-melt adhesive. The manner of joining the three members is in a discontinuous pattern of lines, spots, helixes, etc. so as not to inhibit water vapor from passing through the breathable film 3a. The amount of the hot-melt adhesive to be applied between adjacent members is preferably 0.5 to 7 g/m² for securing sufficient adhesion among the members while retaining the water vapor permeability and a comfortable texture of the laminated sheet. The application methods include slot spraying, curtain spraying, spiral spraying, melt blowing, gravure coating, die coating, and the like.

As shown in FIG. 2(a), a pair of cuffs (or flaps) 8 made of a liquid-resistant or liquid-impermeable and breathable material are provided on longitudinal sides of the topsheet 2. Each cuff 8 has its one end fixed to the topsheet 2 over the length of the topsheet 2, with the other end free. An elastic member 81 is fixed in its flat-out stretched state to each cuff 8 in the vicinity of its free end, whereby the cuffs 8 stand upright to present barriers against the liquid flowing in the lateral direction.

In the backsheet 3, the two nonwoven materials 3b and 3c extend outward from the front and rear edges of the breathable film 3a, and the extended parts are folded back on the topsheet 2 side. The folded parts of the nonwoven materials 3b and 3c in the front and rear waist opening portions are positioned on the absorbent member 4 as shown in FIG. 2(b). A plurality of elastic members 51a and 51b are fixedly disposed between the folded parts of the nonwoven materials 3b and 3c over the width of the backsheet 3 in their stretched state. The elastic members 51a and 51b are disposed such that their ends meet with an overlap when the side ends A1 and A2 of the front body portion A and the side ends B1 and B2 of the rear body portion B are respectively joined together. In this manner there are formed substantially continuous loop of gathers encircling near the waist opening 5 of the diaper 1.

As shown in FIGS. 2(a) and 2(b), the two nonwoven materials 3b and 3c extend outward from both longitudinal sides of the breathable film 3a, and the extended parts are provided with elastic members 61a and 61b. Each of the elastic members 61a and 61b is composed of a central part 61a' or 61b' and side parts 61a" or 61b" which are extensions from both ends of the respective central part. The central parts 61a' and 61b' are disposed across the crotch portion C of the diaper 1, and the side portions 61a" and 61b" are along the curves of the crotch portion C. The elastic members 61a and 61b are held between the two nonwoven materials 3b and 3c with their side portions 61a" and 61b" being fixed in their stretched state by an appropriate means. When the side ends A1 and A2 of the front body portion A and the side ends B1 and B2 of the rear body portion B are joined together, respectively, the ends of the elastic member 61a and those of the elastic member 61b meet with an overlap to make a substantially continuous loop of gathers encircling near the leg openings 6 of the diaper 1.

As shown in FIGS. 2(a) and 2(b), elastic members 71a and 71b are also provided in body portions D positioned between the front and rear ends and the curved portions (the crotch portion C) of the diaper 1 along the width direction of the backsheet 3. These elastic members are disposed across the absorbent member 4 in the front and rear body portions A and B, being fixed in their stretched state between the two nonwoven materials 3b and 3c. They are disposed such that their ends meet with an overlap when the side ends A1 and A2 of the front body portion A and the side ends B1 and B2 of the rear body portion B are respectively joined together. There are thus formed loop of gathers in the body portions D in the front and rear body portions A and B which substantially continuously encircle a wearer's body as shown in FIG. 1.

The elastic members 51a, 51b, 61a, 61b, 71a, 71b and 81 are preferably bands or strings made of natural rubber, polyurethane resins, foamed urethane resins, and the like.

As shown in FIG. 1, the backsheet 3 has on the rear body portion B thereof a prescribed pattern 10 printed in multicolor. The pattern can include letters, figures, symbols and combinations thereof. The pattern 10 is printed on the exterior side of the breathable film 3a on which the first nonwoven material 3b is to be superposed.

The pattern 10 has a red area 10a, a green area 10b, a yellow area 10c, a deep blue area 10d, and a light blue area 10e.

Printed on the breathable film 3a, the pattern 10 is to be viewed through the two nonwoven materials 3b and 3c. The view through the nonwoven materials is less clear than without the nonwoven materials. The present inventors have studied for minimizing the reduction in clearness of the print. They have found in their study that a colorimetric system is an effective measure for evaluating the clearness of the printed colors. As a result of their further study, it has been found that, in the parameters representing the colorimetric system, the L* value representing lightness and the C* value representing chroma are more important than the h* value.

More specifically, it has been ascertained that the pattern 10 can be seen clearly through nonwoven material, even through two sheets of nonwoven material as in the above-described embodiment, when the printed area of the breathable film has an L* value of 10 to 93, preferably 20 to 90, still preferably 30 to 80, and a C* value of 20 to 120, preferably 50 to 120, still preferably 60 to 120, as measured with a color difference meter. In particular, when 50% or more, especially 70% or more, of the total area of the printed area (pattern 10) on the breathable film 3a satisfies the above-specified L* and C* conditions, the pattern 10 exhibits clear visibility even through the two pieces of nonwoven material 3b and 3c. It is the most preferred as a matter of course that the ratio of the area that satisfies these conditions be 100%. If the L* value is smaller than 10, the colors are too dark, making multicolor printing meaningless. If the L* value is greater than 93 or if the C* value is smaller than 20, the pattern will be blurred when seen through the nonwoven materials 3a and 3b and is not preferred by consumers. As for the C* value, the higher, the more preferred, but 120 may be the practical upper limit.

The non-printed area of the breathable film 3a, i.e., the background tends to suffer from yellowing by the action of light or heat during storage, causing reduction of the clearness of the pattern 10 printed in multicolor. In order to prevent this from happening, it is desirable that the background be made to have a minus number up to zero as a b* value, i.e., blue tinged beforehand. A preferred b* value of the background is from −5 to 0.

The L*, C*, and b* values are measured with a color difference meter. In the present invention, the measurement was made with a color difference meter SZ-Σ80 (trade name, supplied by Nippon Densyoku Kogyo K.K.) by using the CIE standard illuminant $D_{65}$ (light beam diameter: 6 mm) under a viewing condition of 10° and illumination and light-receiving conditions of 0/45°. A sample was put on a 5 mm or thicker stack of non-printed breathable sheets, and the reflected light was measured.

In order to secure clearness of the pattern 10 even when seen through the nonwoven materials 3b and 3c, it is necessary not only for the printed pattern 10 itself to be clear enough but for the nonwoven materials 3b and 3c to have sufficiently high light transmittance. A light transmittance is represented by a ratio of the intensity of light incident on an object to that of transmitted light. The two nonwoven materials 3b and 3c should have a total luminous transmittance of 40 to 83%, preferably 50 to 75%, still preferably 60 to 75%. If the transmittance is less than 40%, the pattern 10 may have poor visibility through the nonwoven materials even though the L* and C* values fall within the above-described respective ranges, which will lose consumers acceptance. Existence of a nonwoven material(s) having a transmittance exceeding 83% will have no substantial influence on the visibility of the pattern 10.

The light transmittance is measured with a reflectance-transmittance meter HR-100 (trade name, supplied by Murakami Shikisai Kenkyusyo K.K.). A CIE standard illuminant A was used, and a total luminous transmittance $T_t$ was measured on 10 arbitrary points of a sample to obtain an average.

The transmittance of the nonwoven materials 3b and 3c can be increased by decreasing their basis weight, but too small the basis weight tends to fail to provide the backsheet 3 with a satisfactory texture or feel. For securing clearness of the pattern 10 in good balance with texture or feel of the backsheet 3, it is preferred for the nonwoven material(s) superposed on the breathable film 3a to have a total basis weight of 20 to 50 g/m$^2$, particularly 30 to 45 g/m$^2$.

The transmittance of the nonwoven materials 3b and 3c can also be improved by reducing their thickness, but such may result in the same discomfort to a user as with the reduced basis weight. In order to obtain clearness of the pattern 10 in good balance with texture or feel of the backsheet 3, it is preferred for the nonwoven material or a plurality of nonwoven materials which is/are superposed on the breathable film 3a to have a total thickness of 0.5 to 3.0 mm, particularly 0.7 to 2.0 mm before laminating. The term "thickness" of the nonwoven material(s) as referred to here is a thickness of a nonwoven material before being superposed on the breathable film 3a, spread flat on a horizontal mount with a 120 mm-side square plate weighing 50 g put thereon. Where two or more sheets of nonwoven material are superposed as in the presently described embodiment, the individual thicknesses measured separately are added up to obtain the total thickness.

Materials fabricating the nonwoven materials 3b and 3c include fibers of thermoplastic resins, such as polyolefins (e.g., polyethylene and polypropylene), polyesters (e.g., polyethylene terephthalate), and polyamides, and conjugate fibers, such as core-sheath types and side-by-side types, made of two or more of these resins. The nonwoven materials 3b and 3c may be either the same or different. It is preferred for the fibers constituting the nonwoven materials 3b and 3c to have a small fineness for providing the backsheet 3 with a satisfactory texture or feel, specifically of from 1.0 to 4.0 dtex, particularly 1.5 to 3.5 dtex. Finer fibers than 1.0 dtex are difficult to make, only serving to increase the cost of production.

The nonwoven materials 3b and 3c can be produced in ordinary processes such as an air-through bonding process, a melt-blowing process, a heat rolling process, a spun-bonding process, and a suction heat bonding process.

While the nonwoven materials 3b and 3c are preferably white or very lightly tinged, it may be colored as long as the clearness of the pattern 10 or the appearance of the diaper 1 are not impaired.

The breathable film 3a is preferably a microporous film obtained by forming a molten resin composition comprising a polyolefin resin, for example, a filler, and a third component into sheeting, which is stretched at least uniaxially. The polyolefin resins include low-to-high density polyethylene, linear-low-density polyethylene, polypropylene, polybutene, and mixtures thereof.

The moisture vapor transport rate of the breathable film 3a is represented as a water vapor transmittance rate measured in accordance with JIS Z0208, provided that a sample is kept at 32° C. for 1 hour before measurement. A breathable film 3a having a moisture vapor transport rate of 0.5 to 4.0 g/(100 cm$^2$·hr), particularly 0.5 to 2.5 g/(100 cm$^2$·hr), is preferred for letting the internal humidity escape to give comfort to a wearer and for preventing body fluids from leaking through pinholes.

It is preferred for the breathable film 3a to have a basis weight of 10 to 50 g/m$^2$, particularly 15 to 30 g/m$^2$ for retaining sufficient strength and giving agreeable feeling.

A unitary laminate of the breathable film 3a and the two nonwoven materials 3b and 3c can be subjected to embossing to increase the adhesion among the members while improving the texture. The engraved roll used for embossing includes a metallic roll having a large number of bosses in various patterns. The engraved roll is preferably capable of being heated. The back-up roll, used in combination with the engraved roll, should have a specific surface hardness, which is preferably a durometer hardness of 70 to 94° measured in accordance with JIS K7215. The material of the back-up roll is not limited, provided that the above-specified surface hardness is secured.

Multicolor printing on the breathable film 3a can be carried out by, for example, flexographic printing or gravure printing. Any other printing techniques, if appropriate, can be utilized. Flexographic printing is a technique in which an object to be printed is clinging to an impression drum while running on a plate cylinder and therefore undergoes little stretching. Therefore, it is suited for multicolor printing on a thin and stretchy material like the breathable film 3a.

On printing, the micropores of the breathable film 3a, through which water vapor can escape, are clogged with ink to reduce the water vapor permeability. Hence, the printing area is preferably as small as is consistent with the purpose of printing. The pattern to be printed is by no means limited in color, design or theme.

The present invention is not limited to the aforementioned embodiment, and various modifications can be made therein. For example, the two nonwoven materials 3b and 3c, which constitute the backsheet 3 in combination with the breathable film 3a, can be replaced with a single sheet of nonwoven material. All the breathable film 3a and the nonwoven materials 3b and 3c used in the above-described embodiment may have the same shape.

The present invention is not limited to a pants type disposable diaper as referred to above as a particular embodiment of absorbent articles and includes other types of disposable diapers, adult incontinence pads, sanitary napkins, and any other absorbent articles.

The present invention will now be illustrated in greater detail by way of Examples. It should be understood that the following Examples are presented as being exemplary of the present invention and are not construed as limiting. Unless otherwise noted, all the parts and percents are by weight.

EXAMPLES 1 AND 2 AND COMPARATIVE EXAMPLES 1 AND 2

(1) Preparation of Breathable Film

Linear low-density polyethylene (UZ2520F, available from Mitsui Chemical K.K.), calcium carbonate (Escalon #2000, available from Sankyo Seifun K.K.), an ester composition (Exceparl TM20-AS, available from Kao Corp.), and stearic acid (Lunac S-40, available from Kao Corp.) were kneaded and pelletized at a ratio of 37:58:4:1 in percent by weight in a twin-screw kneading machine. The pellets were molded into sheeting by a blown-film extruder, and the blown film was stretched 2.3 times on a roll stretching machine at a stretching temperature of 50° C. to obtain a microporous breathable film. The resulting breathable film had a basis weight of 20 g/m$^2$ and a moisture vapor transport rate of 1.8 g/(100 cm$^2$·hr).

The breathable film was printed, on one side thereof, with the pattern 10 shown in FIG. 1 in multicolor by flexographic printing. As previously mentioned, the pattern 10 had a red area 10a, a green area 10b, a yellow area 10c, a deep blue area 10d, and a light blue area 10e. The pattern 10 was printed on the breathable film of continuous length at such an interval that, when the film was cut to lengths and assembled into diapers, the pattern might be positioned on the rear half of the diapers. The L* and C* values of each color of the printed pattern measured with a color difference meter SZ-Σ80 are shown in Table 1 below. The L*, a*, b*, and C* values of the background were 96, 0, −0.1, and 0.1, respectively.

(2) Preparation of Nonwoven Material

Core-sheath type conjugate fibers made of polyethylene terephthalate as a core and polyethylene as a sheath were made into nonwoven material by an air-through process. Nonwoven material made of fibers having a fineness of 3.1 dtex was used as the nonwoven material 3b shown in FIGS. 1, 2(a) and 2(b), and one made of fibers having a fineness of 2.0 dtex was used as the nonwoven material 3c.

(3) Preparation of Laminated Sheet (Backsheet)

A laminated sheet was prepared by adhering the breathable film obtained in (1) above and the two nonwoven materials 3b and 3c obtained in (2) above with a hot-melt adhesive comprising a styrene-butadiene-styrene block copolymer as a base polymer, which was applied in parts on either one of the two members to be joined in an amount of 5 g/m$^2$. Embossing was not conducted. The total basis weight, the total thickness, and the total luminous transmittance of the two nonwoven materials before laminating are shown in Table 1.

(4) Preparation of Pants Type Disposable Diaper

Pants type disposable diapers shown in FIGS. 1, 2(a) and 2(b) were produced by using the laminated sheet prepared in (3) above as a backsheet and other members commonly used in disposable diapers.

(5) Evaluation

The resulting diapers were evaluated and graded for clearness of the printed pattern and the texture or feel according to the following standards.

Clearness of Printed Pattern:

The clearness of the printed pattern was observed by a panel of five members with their naked eyes and rated on an A-to-D scale. Those patterns seen as sufficiently clear were rated "A" or "B" (A is better than B), and those seen as insufficiently clear were rated "C" or "D" (D is the poorest).

Texture and feel:

The feel of the surface of the diaper was organoleptically evaluated by a panel of five members and rated on an A-to-D scale. The diapers feeling agreeable to the touch were rated "A" or "B" (A is better than B), and those feeling insufficiently agreeable to the touch were rated "C" or "D" (C is better than D).

TABLE 1

| | Breathable Film | | | | Nonwoven material | | | Diaper | |
|---|---|---|---|---|---|---|---|---|---|
| | Color | L* Value | C* Value | Basis Weight (g/m$^2$) | Moisture Vapor Transport Rate g/(100 cm$^2$ · hr) | Transmittance (%) | Basis Weight (g/m$^2$) | Thickness (mm) | Clearness of Pattern | Texture & Feel |
| Example 1 | deep blue area | 60.7 | 52.5 | 20 | 1.8 | 64 | 40 | 1.2 | B | A |
| | light blue area | 79.3 | 25 | | | | | | | |
| | yellow area | 90 | 92.6 | | | | | | | |
| | red area | 55.7 | 79.4 | | | | | | | |
| | green area | 73.6 | 70.5 | | | | | | | |
| Example 2 | the same as in Example 1 | | | 20 | | 73 | 30 | 1.0 | B | B |
| Comparative Example 1 | deep blue area | 87 | 13 | 20 | | 64 | 40 | 1.2 | D | A |
| | light blue area | 78 | 10 | | | | | | | |
| | yellow area | 90 | 18 | | | | | | | |
| | red area | 95 | 10 | | | | | | | |
| | green area | 73.6 | 19 | | | | | | | |
| Comparative Example 2 | the same as in Example 1 | | | 20 | | 85 | 17 | 0.2 | A | D |

As is apparent from the results in Table 1, the diapers of Examples, in which the printed area of the breathable film has L* and C* values falling within the respective specific ranges, and the nonwoven material has a light transmittance within a specific range, satisfy both the requirements of the print visibility and the texture and feel to the touch, whereas the comparative diapers do not meet both the requirements. In Examples 1 and 2, the ratio of the printed area that satisfied the requirements as to the L* value and the C* value was 70% or more in the total printed area.

As described above, the absorbent article of the present invention which has a multicolor printed area is satisfactory in both clearness of the printing and texture or feel.

The invention having been thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbent article comprising a liquid-permeable topsheet, a liquid-impermeable backsheet, and a liquid retentive absorbent member interposed between the topsheet and the backsheet, wherein said backsheet comprises a laminated sheet composed of a breathable film printed with a multicolor pattern, a first nonwoven material and a second nonwoven material laminated on said first nonwoven material, the first nonwoven material being superposed on the printed side of said film, an elastic member is fixedly disposed between said first and second nonwoven materials, a total basis weight which is a sum of a basis weight of said first nonwoven material and a basis weight of said second nonwoven material is 20 to 50 g/m$^2$, and a total thickness which is a sum of a thickness of said first nonwoven material and a thickness of said second nonwoven material before laminating said first and second nonwoven materials is 0.5 to 3.0 mm, the printed area of said film has an L* value of 10 to 93 and a C* value of 20 to 120 as measured with a color difference meter, a total light transmittance of said first nonwoven material and said second nonwoven material is 40 to 83%; and nonprinted background areas on the printed side of said breathable film have a b* value of 0 to −5.

2. The absorbent article according to claim 1, wherein said b* value is less than 0 and greater than or equal to −5.

3. The absorbent article according to claim 1, wherein 50% or more of the total area of the printed area on the breathable film satisfies the requirement of an L* value of 10 to 93 and a C* value of 20 to 120 as measured with a color difference meter.

4. The absorbent article according to claim 1, wherein the moisture vapor transport rate of the breathable film is 0.5 to 4.0 g/(100 cm$^2$·hr) measured in accordance with JIS Z0208.

* * * * *